United States Patent [19]

Kerschmann

[11] Patent Number: 4,960,330
[45] Date of Patent: Oct. 2, 1990

[54] IMAGE RECORDING APPARATUS

[76] Inventor: Russell L. Kerschmann, 3 Concord Ave. #32, Cambridge, Mass. 02138

[21] Appl. No.: 217,669

[22] Filed: Jul. 11, 1988

Related U.S. Application Data

[63] Continuation-in-part of Ser. No. 755,429, Jul. 16, 1985, abandoned.

[51] Int. Cl.$^5$ .............................................. G01N 1/30
[52] U.S. Cl. ..................................................... 356/36
[58] Field of Search .......................... 356/36; 352/131; 358/93

[56] References Cited

U.S. PATENT DOCUMENTS

| | | | |
|---|---|---|---|
| 3,884,563 | 5/1975 | Evans et al. | 352/131 |
| 3,973,827 | 8/1976 | Uetake | 350/527 |
| 4,377,958 | 3/1983 | Leighton | 83/411 R |
| 4,412,961 | 11/1983 | DiBiasi et al. | 356/448 |
| 4,558,438 | 12/1985 | Jones et al. | 367/71 |

FOREIGN PATENT DOCUMENTS

0139424  5/1985  European Pat. Off. .
2074749 11/1981  United Kingdom .

OTHER PUBLICATIONS

LKB Instruction Manual, "Target Marker 11870", pp. 5–13.
LKB Instruction Manual, "LKB 11800 Pyramitome", pp. 5–25.
Foote, Stephen L. et al., Journal of Neuroscience Methods, vol. 3 (1980), pp. 159–173.
Gras, Heribert, Computer Programs in Biomedicine, vol. 18 (1984) pp. 217–226.
Gras, Heribert et al., Computer Programs in Biomedicine, vol. 17 (1983) pp. 145–156.
Hegre, Erling S. et al., Stain Technology, vol. 21, No. 4, Oct. 1946 pp. 161–164.
Johnson, Ellen M. et al., Computers and Biomedical Research, vol. 16, pp. 79–87 (1983).
Leighton, Stephen B. et al., Abstracts from MBL General Meetings, Sectionless Sectioning: A Systematic Method for Scanning Electron Microscopic Examination of Embedded Tissue, pp. 444–445.
Livingston, Robert B. et al., Trans. AM. Neurol. Assoc. (1976), vol. 101 pp. 99–101 (Quantitative Brain Cinemorphology).
Postlethwait, S. N. et al., Journal of the SMPTE, vol. 73, (Aug. 1964) pp. 629–631.
Postlethwait, S. N., Turtox News, vol. 40, No. 4, (Apr. 1962) pp. 98–100.
Street, Cameron H. et al., Journal of Neuroscience Methods, vol. 7, (1983) pp. 359–375.
Whimster, W. F. et al., Am. Rev. Respiratory Disease, vol. 129, pp. 985–988 (1984).
Wong, Yu-Man Matthew et al., Computer Reconstruction of Serial Sections, Departments of Biometry and Anatomy, Medical University of South Carolina, (May 17, 1983), pp. 580–586.

*Primary Examiner*—Richard A. Rosenberger
*Attorney, Agent, or Firm*—Fish & Richardson

[57] ABSTRACT

Image recording apparatus comprising a block in which an object is embedded in fluorescence stained condition, means for holding said block, means for cutting slices from said block to form successively deeper faces on the block, and magnification and recording means, including a computer and either a microscope or a scanning laser positioned to receive, by means of said microscope or said scanning laser, images of said successive faces on the block, record said images, and store said recorded images in said computer.

7 Claims, 1 Drawing Sheet

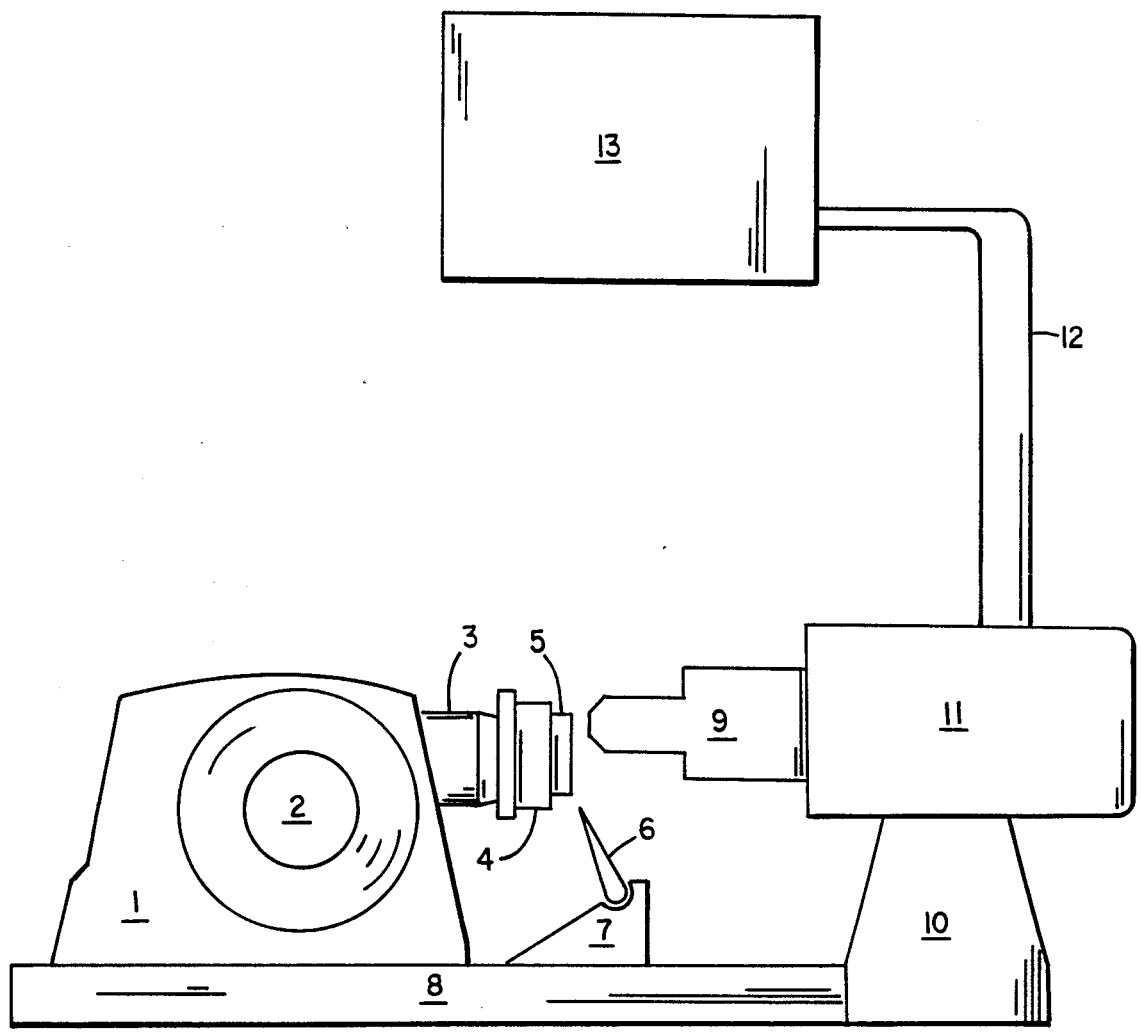
FIGURE

IMAGE RECORDING APPARATUS

BACKGROUND OF THE INVENTION

This application is a continuation-in-part of Kerschmann U.S. patent application Ser. No. 755,429, filed July 16, 1985, now abandoned.

This invention relates to recording visual images of, e.g., pathology samples.

Most examination of tissue on the microscopic level is carried out by illuminating a thin tissue slice cut from the surface of a block, to give an effectively two-dimensional image. Information about three-dimensional structures in the tissue is obtained by examining and/or photographing successive slices, which are commonly mounted on glass slides. The tissue is either stained prior to embedding in the block, or mounted slices stained on the slides.

SUMMARY OF THE INVENTION

In general, the invention features image recording apparatus including a block in which an object is embedded in fluorescence stained condition; means for holding the block; means for cutting slices from the block to form successively deeper faces on the block; and magnification and recording means, including a computer and either a microscope or a scanning laser positioned to receive images of the successive block faces, record the images and store and process the images in the computer.

In preferred embodiments, the visual recording means is a video camera which receives images through a microscope (preferably a fluorescence microscope) or alternatively, a scanning laser composed of a laser, scanning optics, and a detector, connected to a computer capable of storing the images, and the apparatus includes a screen for displaying the stored images. Preferably the computer is also capable of creating on the screen a three-dimensional reconstruction of a portion of the object from the stored images. Preferably the embedded object is a piece of human or animal tissue, and the embedding process includes the use of tissue-staining dyes and/or infiltrating and/or embedding additives for providing sharper images, as is discussed in greater detail below. (As used herein, the term "staining" refers to treating tissue with a dye which associates with the tissue on a molecular level. "Infiltration" refers to treating the tissue with increasing concentrations of a substance which permeates the tissue and then hardens. "Embedding" refers to immersing the infiltrated tissue in a substance (which is usually the same as the infiltrating substance) which is then hardened to form the block; the embedding substance thus serves to provide rigid support and to facilitate the cutting process.)

The invention provides rapid, highly automated recording and storage of structural information on the internal architecture of the embedded object, without the inconvenient, time-consuming handling and storage of individual cut sections. These advantages flow in part from the fact that it is the image on the block face, rather than each cut section, which is recorded following each cut. Successive images can be recorded with the microscope or laser detector and knife held stationary throughout the process. The stored images readily lend themselves to computerized image processing, e.g., three dimensional image reconstruction, useful in many applications, particularly human and veterinary pathology analysis.

Other features and advantages of the invention will be apparent from the following description of the preferred embodiments thereof, and from the claims.

DESCRIPTION OF THE PREFERRED EMBODIMENTS

The drawing will first be described.

DRAWING

The FIGURE is a diagramatic representation of apparatus of the invention.

STRUCTURE

Refering to the FIGURE, the general elements of the apparatus are the microtome components (1-8 in the FIGURE); the microscope components or alternatively the laser and scanning optics components (9-10 in the FIGURE); and the electronic components (11-13 in the FIGURE).

Turning first to the microtome components, there is shown conventional microtome including base 8, body 1, motor drive 2, reciprocating bar 3, tissue block holder 4, holding tissue block 5, and metal or glass knife blade 6, held in knife holder 7.

The base 10 supports the microscope optics/laser and scanning optics 9 and the video camera/scanning laser electronics 11. Focussing of the microscope/scanning laser optics is accomplished by extension or retraction of part or all of the microscope/scanning laser optics. Video camera/scanning laser electronics 11, connects via connecting cable 12 to computer 13.

Before describing the operation of the illustrated apparatus, there will be described various methods of minimizing "noise" in the form of out-of-focus images of tissue which are deeper in the block than the surface image which is being recorded; the less the deeper tissue is "visible" to the image recording means, the cleaner and more noise-free will be the recorded surface image.

QUENCHING

One method of minimizing such noise, while providing tissue/block contrast, is to stain the tissue with a fluorescent dye, and then infiltrate the tissue with, and include in the embedding material (generally a plastic polymer, as discussed in more detail below), a fluorescence quencher (e.g. ethyl iodide) which inhibits emission by the dye; the microscope or scanning laser in such a system emits light which illuminates the block face at the absorbance wavelength of the fluorescent dye, and views or detects by scanning images at the emission wavelength (generally in the visible range). The quencher inhibits excitation of the dye in the tissue deep in the block to a greater degree than the dye in the tissue at the surface, which has had some of the surrounding quencher removed by the microtome knife. Any suitable conventional fluorescence quenchers and dyes, e.g., fluorescien or Hoechst dye 33258 (discussed further below) can be used in the fluorescent dye/quencher method. Alternatively, instead of adding a quencher to the embedding material, the infiltrating-/embedding material itself can be chemically modified to provide quenching.

EXCITATION BLOCKING

Another noise minimization method employs compounds which absorb the ultraviolet or shortwavelength visible light normally used for excitation, in conjunction with a fluorescent dye which maximally absorbs at a wavelength near the absorption maximum of the excitation blocker. For example, the method can employ a dye which maximally absorbs in the ultraviolet range at about 340 nm and an excitation blocker which also maximally absorbs at about 340 nm. This system works as follows. UV light of a wavelength of 340 nm illuminates the block face and is absorbed by and excites the fluorescent dye in the tissue at the block surface. Deeper in the block, the excitation blocker absorbs the UV light (to an extent which increases with increasing depth), inhibiting absorption and therefore excitation and emission by the dye deeper in the block. A suitable dye/UV absorber pair is Hoechst dye 33258 (Bisbenzimide,2'-(4-hydroxyphenyl)-5-(4-methyl-1-piperazinyl)-2,5-bi-1H-benzimidazole trihydrochloride pentahydrate), which maximally absorbs at 343 nm; and the UV absorber 2-(2'-hydroxy-5-methylphenyl)bensotriazole (described in Encyclopedia of Chemical Technology ed. Kirk-Othmer, John Wiley & Sons), which maximally absorbs at about 339 nm; the latter compound also advantageously inhibits embedding material degradation by ambient light.

TRANSMITTANCE BLOCKING

Another noise-minimization method involves the inclusion in the infiltration and embedding material of a dye which, unlike the quencher (which interferes with the mechanism of fluorescence emission), and compounds which block the entrance of excitation light, blocks light transmittance across a broad range of visible light wavelengths and this prevents emissions from deep in the block from reaching the surface. Black dyes are suitable for this purpose; examples are various formulations Orasol Black (e.g. RL and CN, CIBA GEIGY Corp.).

COMPLEMENTARY DYES

An additional noise-inhibiting method involves the use of two different fluorescent dyes, the first of which stains the tissue and emits at a wavelength which is absorbed by and excites the second, which is added to the infiltrating and embedding materials. Excitation of the first dye in tissue present at the surface of the block will simply cause the emission of light of the emission wavelengths to provide a recordable image. Excitation of the first dye in tissue deep in the block, however, results in some of the emitted light being asorbed by the second dye along the emitted light's path to the surface, reducing undesired emission from within the block. In addition, this indirect excitation of the second dye causes light emission at a wavelength different from the emission wavelength of the first dye; the computer associated with the microscope or scanning laser can be programmed to subtract from the image light of this second wavelength, effectively increasing the contrast of the image.

COMPUTER IMAGE ENHANCEMENT

Another method of reducing noise from images within the block involves enhancing the image using appropriate computer software. The ability of computer programs to enhance the surface image compared to deeper images can be based on the differences in sharpness between surface and deeper images, resulting from light scattering which causes blurring within the block but not at the surface. Software for providing such processing exists and is used, e.g., for removing cloud cover from aerial photographs, as described in Lim, "Image Enhancement" in Digital Image Processing Techniques, Ekstrom, ed., Academic Press, Inc., 1984. A number of commercial companies sell image processing software, e.g., Imaging Technology Incorporated, Woburn, MA.

Another powerful computational technique for eliminating images from deep in a block is that of digital subtraction. This method has been employed in the field of radiology to enhance angiographic images of vessels in the heart, brain and other organs, as described in Digital Radiography: A Focus on Clinical Utility, Price, et.al. ed., Grune & Stratton, 1982. In this technique, one digitized image, called a "mask", is subtracted point by point from a second image containing features which are to be enhanced.

As applied to the suppression of deep images in a block containing a tissue sample, the image containing the information one wishes to enhance is the image at the surface of the block. This image is the sum of the image of the cut surface of the tissue plus undesirable images transmitted to the surface from below. In order to remove these deep images, the mask is generated from the next deeper block face, which is revealed after sectioning of the block. Before subtraction is performed the mask can be preprocessed to restore the blurring and attenuation of its signal that existed prior to sectioning, caused by the overlying layer of tissue and embedding material, and by the fact that the deep images arise in a zone that is not in the plane of focus of the microscope objective lens or of the scanning laser. These parameters may be calculated according to known methods, from the diffusion and extinction coefficients of the embedding material, and the optical properties of the microscope or scanning laser, respectively.

It may be desirable in some instances to employ several of the above-described noise reduction methods in conjunction with each other, e.g., a UV absorber, a quencher, a visible light absorber, and computerized image enhancements can all be used in the same system.

OPERATION

The first step in using the invention is the fixing, staining, and infiltrating/embedding of the tissue. Such tissue processing is carried out using the materials described above, according to standard en bloc staining and embedding techniques. Preferably, the embedding material is a polymeric plastic material, e.g., the glycomethacrylates commonly used in pathology tissue embedding for light microscopy.

After staining and embedding, the tissue block 5 (referring to the FIGURE) is inserted into tissue block holder 4 in the desired orientation, and the microtome drive 2 activated to cut tissue slices from the block with knife 6 while reciprocating bar 3 moves up and down and is advanced after each cut by the automatic microtome advancing mechanism which is standard on many microtomes, by a distance corresponding to the thickness of one section. The slices cut from the block can be discarded, or some or all retained for additional processing (e.g., staining with any number of dyes) for conventional examination.

In the case of using the invention in the fluorescence microscope mode, after each cut, fluorescence epiillumination light emitted by the microscope 9 illuminates the surface of block 5, exciting the fluorescent dye in the tissue, and video camera 11 records the fluorescent surface image, and transmits the image to computer 13 for storage and processing. Alternatively, the focussed laser beam, emitted by the scanning laser optics 9, scans the surface of the block 5, either by the sweeping of the beam across the block under the control of the scanning laser optics, or by the rotation, translation, or combination thereof, of the block under a stationary or moving laser beam; the variation in intensity of the spot of laser light as it moves upon the surface of the block is detected by the scanning laser electronics 11 and the resulting electrical signal is transmitted to the computer for image reconstitution, storage and processing.

It as apparent from the foregoing that magnification according to the invention is accomplished in either of two different ways: by means of a microscope, or by means of a scanning laser which does not require, and in fact takes the place of, a microscope. The scanning laser beam, because of the extremely small diameter of the beam, is capable of "seeing" the same, or greater, level of detail as the microscope. This fine laser-detected information is then converted digitally into human user- or machine-viewable enlarged images.

In both the microscopic and scanning laser magnification embodiments of the invention, the en bloc fluorescent staining is critical, allowing for resolution and contrast essential for the formation of useful images.

APPLICATIONS

The invention provides the capacity to automatically record and store large numbers of successive tissue images, with virtually no human handling of the tissue once the block has been mounted on the microtome. The storage of the images in a computer permits software-controled manipulation of the images in a variety of ways. For example, the images of consecutive sections of the tissue will normally be stored, and the computer programmed, so that the person (e.g., pathologist) viewing the stored images can display them in rapid succession to effectively "melt" through the tissue on the display screen. In the case of a biopsy, this will result in the complete sampling of the tissue. In addition, the computer can be programmed to construct, from the stored images, a three-dimensional reconstruction of all or a portion of the tissue, and to manipulate that image by rotating it to any desired orientation and/or by choosing to view any cross-section of the reconstructed image.

The pathology applications of the invention are virtually limitless. Any tissue which was previously capable of being examined by conventional two-dimensional microscopy can be analysed using the invention.

Examples of problem pathology specimens that can be better examined, and entirely new approaches to tissue analysis possible with the invention, are:

(1) Tissues containing a few very small structures which are critical in reaching a diagnosis. These could be missed by conventional histology processing due to sampling errors but would be detectable through the complete sampling feature of the invention, e.g., granulomas (sarcoid of the lung, regional enteritis), microorganisms, multinucleated giant cells (giant cell arteritis), small foci of invasion by malignant tumors (carcinoma of the uterine cervix, malignant melanoma), or small foci of metastatic tumor in lymph nodes. The capacity to use the invention to examine the entire tissue may permit the taking of smaller biopsies in some cases.

(2) Specimens which demand that special attention be paid to the margins of resection to assure that no disease (e.g., malignant tumor) has been left in the patient. Basal cell carcinomas of the skin can often occur in locations (e.g., the face) where it is desirable to spare as much of the adjacent normal tissue as possible; in attempting to accomplish this, the surgeon may cut through the edge of the lesion, resulting in a specimen with tumor present at one small portion of its edge. Through sampling error, this important feature could be missed, but would be detected by the invention.

(3) The diagnosis of disorders in which the orientation of the biopsy is critical. This is a recurrent problem in surgical pathology, especially when dealing with small biopsies of mucosal surfaces such as the lining of the bowel, stomach or esophagus. Only a certain plane of section through the tissue, usually one taken perpendicular to the mucosal surface, will permit estimation of the relative proportions of the various tissue components, such as the villus/crypt ratio critical in the diagnosis of non-tropical sprue in the small bowel. The capacity for the invention to rotate the image of the tissue to any desired orientation eliminates this problem.

(4) A situation related to (3) in which optimal diagnosis requires views of a biopsy from two or more different aspects. Only one angle of plane of section can be sampled by conventional methods, which may force a sacrifice of information in some situations, such as in the diagnosis of alopecia from punch biopsies of the scalp where both perpendicular and transverse sections are of value.

(5) Determination of the volume of a microscopic structure may prove to be useful in some cases, but only crude approximations are possible by current methods. For example, the amount of early invasive tumor in the uterine cervix or of the invasive component of malignant melanoma in the skin have important prognostic significance. This measurement could be precisely made by use of the invention and the appropriate computer software.

(6) The capability to produce three dimensional reconstructions of cell nuclei will allow for a more precise determination of the total DNA content, or "ploidy" of the cell. This is a measurement that has important prognostic significance in the treatment of cancer, since tumors composed of cells with unusual chromosome complements have been demonstrated to behave in a more aggressive fashion.

Currently available morphometry instruments have generally failed to produce accurate ploidy analysis from sections because the usual 4–5 micron thick section contains only a portion of a tumor nucleus, the diameter of which may be in the range of 20 microns,or more. Sections made much thicker to include more whole nuclei still present the problem of partial nuclei residing at the two surfaces, introducing noise into the data. In addition, thicker sections present more opportunity for overlap of the images of nuclei, another important source of error. Therefore, for morphometric ploidy analysis, present systems often require that touch preparations be made from fresh tissue, or that formalin fixed tissue be disrupted in order to prepare whole isolated nuclei. The extra processing stepd, for both methods, add delay and complication, and because the actual tissue section is not present in the resulting preparation, these techniques make it impossible to interpret the ploidyj of a particular cell in the context of other tissue structures.

The invention overcomes the problems with ocnventional ploidy determination by digitally reassembling images of the nuclei in the computer. Reconstructions representing partial nuclei, as well as those not meeting other criteria (size, shape, etc.) can be detected and excluded from the ploidy determination. Images of adjacent nuclei which may overlap on two dimensional projection can be more easily separated using a three dimensional reconstruction.

The user of the device can arbitrarily select a portion fo the displayed image for immediate ploidy ansalysis of the cells contained in the selected field, with rapid on-screen or hardcopy depiction of the quantitated data. Large numbers of cells can be analyzed, or the ploidy of individual cells can be determined. The capability for real-time ploidy analysis on images that maintain the actual architectural relationships of tumor cells to normal tissue structures will prove extremely valuable in the formulation of diagnosis and prognosis.

(7) Finally, the opportunity offered by the invention to study the three-dimensional arrangement of the various components of a pathologic lesion may revel higher level diagnostic features hitherto made undetectable by conventional two-dimensional techniques. Other embodiments are within the following claims.

I claim:

1. An imagre recording method comprising
   infiltrating an object with and embedding said object in material containing a UV absorber which maximally absorbs at a wavelength near the maximum absorbance wavelength of a first fluorescent dye,
   staining said object with said first fluorescent dye, said dye being characterized by a maximum of absorbance wavelength and a minimum absorbance wavelength,
   embedding said object in a block capable of being cut with a knife,
   cutting a plurality of slices from said block using said knife to form successfully deeper images of said faces on said block,
   receiving, by means of a microscope or scanning laser, successively deeper images of the face of said block,
   recording said successively deeper images of said faces on said block, and
   storing said recorded images in a computer.

2. An image recording method comprising
   staining an object with a first fluorescent dye characterized by a maximum absorbance wavelength and a minimum absorbance wavelength,
   infiltrating said object with and embedding said object in material containing a second fluorescent dye characterized by a maximum absorbance wavelength near the maximum emssion wavelength of said first fluorescent dye,
   embedding said object in a block capable of being cut with a knife,
   cutting a plurality of slices from said block using said knife to form successively deeper images of said faces on said block,
   receiving, by means of a microscope or scanning laser, successively deeper images of the face of said block,
   recording said successively deeper images of said faces on said block, and
   storing said recorded images in a computer.

3. An image recording method comprising staining an object with a first fluorescent dye characterized by a maximum absorbance wavelength and a minimum absorbance wavelength,
   infiltrating said object with and embedding said object in matrial containng a quencher fo said fluorescent dye,
   embedding said object in a block capable of being cut with a knife,
   cutting a plurality of slices from said block using said knife to form successively deeper images of said faces on said block,
   receiving, by means of a microscope or scanning laser, successively deeper images of the face of block,
   recording said successively deeper images of said faces on said block, and
   storing said recorded images in a computer.

4. An image recoroding method comprising staining an object with a first fluorescent dye characterized by a maximum absorbance wavelength and a minimum absorbance wavelength,
   infiltrating said object with and embedding said object in material containing a dye capable of blocking the transmission of visible light through said block,
   embedding said object in a block capable of beibng cut with a knife,
   cutting a plurality of slices from said block using said knife to form successively deeper images of said faces on said block,
   receiving, by means of a microscope or scanning laser, successively deeper images of the faces of said block,
   recording said successively deeper images of said faces on said block, and
   storing said recorded images in a computer.

5. An image recording method comprising
   staining a tissue sample comprising cells containing DNA with a first fluorescent dye charactrerzied by a maximum absorbance wavelength and a minimum absorbance wavelength,
   embedding said object in a block capable of being cut with knife,
   cutting a plurality of slices from said block using said knife to form successively deeper images of said faces on said block,
   receiving, by means of a microscope or scanning laser, successively deeper images of successively deeper images of said faces on said block, and
   storing said recorded images in a computer and determining the ploidy of said cells using said computer.

6. The method of any of claims 1, 2, 3, 4, 5 wherein said visual recording is carried out using a video camera.

7. The method of any of claims 1, 2, 3, 4, 5 wherein said object is a piece of human or animal tissue.

* * * * *

UNITED STATES PATENT AND TRADEMARK OFFICE
CERTIFICATE OF CORRECTION

PATENT NO. : 4,960,330

DATED : October 2, 1990

INVENTOR(S) : RUSSELL L. KERSCHMANN

It is certified that error appears in the above-identified patent and that said Letters Patent is hereby corrected as shown below:

Col. 8, claim 5, lines 55-56, after "deeper images", delete "of successively deeper images" and add --of the face of said block, recording said successively deeper images--.

Signed and Sealed this

Second Day of June, 1992

Attest:

DOUGLAS B. COMER

*Attesting Officer*                   *Acting Commissioner of Patents and Trademarks*